United States Patent
Park et al.

(10) Patent No.: US 10,507,456 B2
(45) Date of Patent: Dec. 17, 2019

(54) METAL OXIDE CATALYST, METHOD OF PREPARING THE CATALYST, AND METHOD OF ALCOHOL USING THE SAME

(71) Applicant: Korea Kumho Petrochemical Co., Ltd., Seoul (KR)

(72) Inventors: Ji Won Park, Daejeon (KR); Yong Hee Yun, Sejong-si (KR); Kyoung Ho Row, Daejeon (KR)

(73) Assignee: KOREA KUMHO PETROCHEMICAL CO., LTD., Seoul (KR)

( * ) Notice: Subject to any disclaimer, the term of this patent is extended or adjusted under 35 U.S.C. 154(b) by 0 days.

(21) Appl. No.: 15/937,033

(22) Filed: Mar. 27, 2018

(65) Prior Publication Data

US 2018/0280940 A1    Oct. 4, 2018

(30) Foreign Application Priority Data

Mar. 28, 2017 (KR) .......................... 10-2017-0039274

(51) Int. Cl.
*B01J 23/755* (2006.01)
*B01J 23/72* (2006.01)
(Continued)

(52) U.S. Cl.
CPC ........... *B01J 23/755* (2013.01); *B01J 23/005* (2013.01); *B01J 23/72* (2013.01); *B01J 35/002* (2013.01);
(Continued)

(58) Field of Classification Search
CPC ........ B01J 23/005; B01J 23/72; B01J 23/755; B01J 35/0013; C01G 3/00; C10G 53/00;
(Continued)

(56) References Cited

U.S. PATENT DOCUMENTS 4,704,480 A    11/1987   Gefri et al.
5,399,537 A *   3/1995   Bhattacharyya ....... B01J 23/005
                                                    423/592.1
(Continued)

FOREIGN PATENT DOCUMENTS

EP    2272587 A1 *  1/2011  ............ B01J 21/005
JP    2010534663 A   11/2010
(Continued)

OTHER PUBLICATIONS

JP 2007031202 (A), Hiyouhaku Juji, et al., Crystalline copper aluminate particulate, particulate-dispersed sol, and method for producing the particulate, English abstract, 2 pages (Year: 2007).*

(Continued)

*Primary Examiner* — Yate' K Cutliff
(74) *Attorney, Agent, or Firm* — Novick, Kim & Lee, PLLC; Jae Youn Kim

(57) ABSTRACT

A metal oxide catalyst involved in a hydrogenation reaction in which a ketone is converted into an alcohol, a method of preparing the metal oxide catalyst, and a method of preparing an alcohol using the same are provided. The metal oxide catalyst has a spinel structure represented by the following Formula 1:

$$XAl_2O_4, \qquad \text{<Formula 1>}$$

wherein X represents nickel or copper.

11 Claims, 2 Drawing Sheets

(51) Int. Cl.
  *C07C 29/145*  (2006.01)
  *B01J 23/00*  (2006.01)
  *B01J 35/00*  (2006.01)
  *B01J 35/02*  (2006.01)
  *B01J 37/04*  (2006.01)
  *B01J 37/00*  (2006.01)
  *C01G 53/00*  (2006.01)
  *C07C 29/143*  (2006.01)
  *C01G 3/00*  (2006.01)
  *B01J 37/08*  (2006.01)

(52) U.S. Cl.
  CPC ......... *B01J 35/0013* (2013.01); *B01J 35/026* (2013.01); *B01J 37/0072* (2013.01); *B01J 37/04* (2013.01); *B01J 37/082* (2013.01); *C01G 3/00* (2013.01); *C01G 53/40* (2013.01); *C07C 29/143* (2013.01); *C07C 29/145* (2013.01); *B01J 37/088* (2013.01); *C01P 2002/32* (2013.01); *C01P 2002/72* (2013.01); *C01P 2004/04* (2013.01); *C01P 2004/62* (2013.01); *C01P 2004/64* (2013.01)

(58) Field of Classification Search
  CPC .. C10G 53/40; C01P 2002/32; C01P 2004/04; C07C 29/132; C07C 29/143; C07C 29/145
  See application file for complete search history.

(56) References Cited

U.S. PATENT DOCUMENTS

| | | | | |
|---|---|---|---|---|
| 5,736,114 A | * | 4/1998 | Barthe | B01D 53/9418 423/213.2 |
| 6,201,160 B1 | * | 3/2001 | Brudermuller | B01J 21/08 502/305 |
| 6,218,335 B1 | * | 4/2001 | Okada | B01J 23/005 423/604 |
| 6,455,464 B1 | * | 9/2002 | Chen | B01D 53/86 502/344 |
| 8,222,460 B2 | * | 7/2012 | Sawrey | C07C 29/145 568/388 |
| 2011/0060169 A1 | * | 3/2011 | Kaizik | B01J 23/26 568/881 |

FOREIGN PATENT DOCUMENTS

| | | | |
|---|---|---|---|
| JP | 5268174 B2 * | 8/2013 | ............... C10G 3/00 |
| KR | 10-1997-0703295 A | 7/1997 | |
| KR | 20000048863 A | 7/2000 | |
| KR | 20100046234 A | 5/2010 | |

OTHER PUBLICATIONS

Faugnawakij, K. et al., Cu-based spinel catalysts $CuB_2O_4$ (B=Fe, Mn, Dr, Ga, Al, $Fe_{0.75}Mn_{0.25}$) for steam reforming of dimethyl ether, 2007, Applied Catalysis A: General, vol. 341, pp. 139-145 (Year: 2008).*

Hasan, MD, et al., Synthesis of stiochiometric nickel aluminate spinel nanoparticles, 2015, American Mineralogist, vol. 100, pp. 652-657 (Year: 2015).*

Kwak, B. K., et al., Preparation and characterization of nanocrystalline $CuAl_2O_4$ spinel catalysts by sol-gel method for the hydrogenolysis of glycerol, 2012, Catalysis Communications, vol. 24, pp. 90-95 (Year: 2012).*

Salhi, N., et al., Steam reforming of methane to syngas over $NiAl_2O_4$ spinel catalyst, 2011, International Journal of Hydrogen Energy, vol. 36, pp. 11433-11439 (Year: 2011).*

* cited by examiner

METAL OXIDE CATALYST, METHOD OF PREPARING THE CATALYST, AND METHOD OF ALCOHOL USING THE SAME

CROSS-REFERENCE TO RELATED APPLICATION

This application claims priority to and the benefit of Korean Patent Application No. 2017-0039274, filed on Mar. 28, 2017, the disclosure of which is incorporated herein by reference in its entirety.

BACKGROUND

1. Field of the Invention

The present invention relates to a metal oxide catalyst, a method of preparing the metal oxide catalyst, and a method of preparing an alcohol using the same.

2. Discussion of Related Art

For a catalyst involved in a reaction in which a ketone is converted into an alcohol, Korean Patent Unexamined Publication No. 10-1997-0703295 discloses a catalyst containing copper on a $SiO_2$-containing carrier in the presence or absence of one or more elements selected from magnesium, barium, zinc, and chromium. However, such a catalyst has drawbacks in that its preparation process is complex, and it has low energy efficiency because such a process is performed under a high-pressure condition.

Also, Registered U.S. Pat. No. 4,704,480 discloses a CuO catalyst as a catalyst for hydrogenating methyl isobutyl ketone to convert the methyl isobutyl ketone into methyl isobutyl carbinol. In this case, such a catalyst has problems in that it is difficult to control generation of heat in hydrogenation reactions, and it has low alcohol yield and selectivity.

As described above, various catalysts involved in a conventional hydrogenation reaction used to prepare an alcohol from a ketone have been proposed. However, the catalysts have problems in that methods of preparing the catalysts are complicated, and, when the catalysts prepared by these methods are used, the catalysts have low process efficiency due to high reaction temperature and pressure, low liquid hourly space velocity, and the like.

SUMMARY OF THE INVENTION

Therefore, the present invention is designed to solve the problems of the prior art, and it is an object of the present invention to provide a metal oxide catalyst capable of improving alcohol yield and selectivity in a hydrogenation reaction in which a ketone is converted into an alcohol, a method of preparing the metal oxide catalyst, and a method of preparing an alcohol using the same.

According to an aspect of the present invention, there is provided a metal oxide catalyst involved in a hydrogenation reaction in which a ketone is converted into an alcohol, wherein the metal oxide catalyst has a spinel structure represented by the following Formula 1:

  <Formula 1> wherein X represents nickel or copper.

According to one exemplary embodiment, a content of the nickel in the metal oxide catalyst may be in a range of 20 to 65% by weight.

According to one exemplary embodiment, a content of the copper in the metal oxide catalyst may be in a range of 20 to 65% by weight.

According to one exemplary embodiment, the metal oxide catalyst may have an average particle size of 100 to 1,000 nm.

According to another aspect of the present invention, there is provided a method of preparing a metal oxide catalyst, which includes: (a) dissolving a nickel or copper precursor and an aluminum precursor in a polar solvent to prepare a precursor solution; (b) pyrolyzing the precursor solution while spraying the precursor solution into a reactor using a carrier gas so as to form a catalyst powder; and (c) transferring the catalyst powder to a storage tank, followed by calcining the catalyst powder in the storage tank to increase a surface area of the catalyst powder.

According to one exemplary embodiment, the polar solvent in step (a) may be distilled water.

According to one exemplary embodiment, the pyrolysis in step (b) may be carried out at a temperature of 600 to 850° C.

According to one exemplary embodiment, the calcination in step (c) may be carried out at a temperature of 350 to 450° C.

According to still another aspect of the present invention, there is provided a method of preparing an alcohol, which includes allowing hydrogen to react with a ketone in the presence of the metal oxide catalyst to convert the ketone into an alcohol.

According to one exemplary embodiment, the ketone may be methyl isobutyl ketone.

According to one exemplary embodiment, the alcohol may be methyl isobutyl carbinol.

According to one exemplary embodiment, the reaction may be carried out at a temperature of 70 to 150° C.

According to one exemplary embodiment, the reaction may be carried out at a pressure of 0.0 to 3.0 barg.

According to one exemplary embodiment, the reaction may be carried out at a liquid hourly space velocity of 0.1 to 1.7 $hr^{-1}$.

According to one exemplary embodiment, the ketone and the hydrogen may be allowed to react at a molar ratio of 1:4 to 8.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
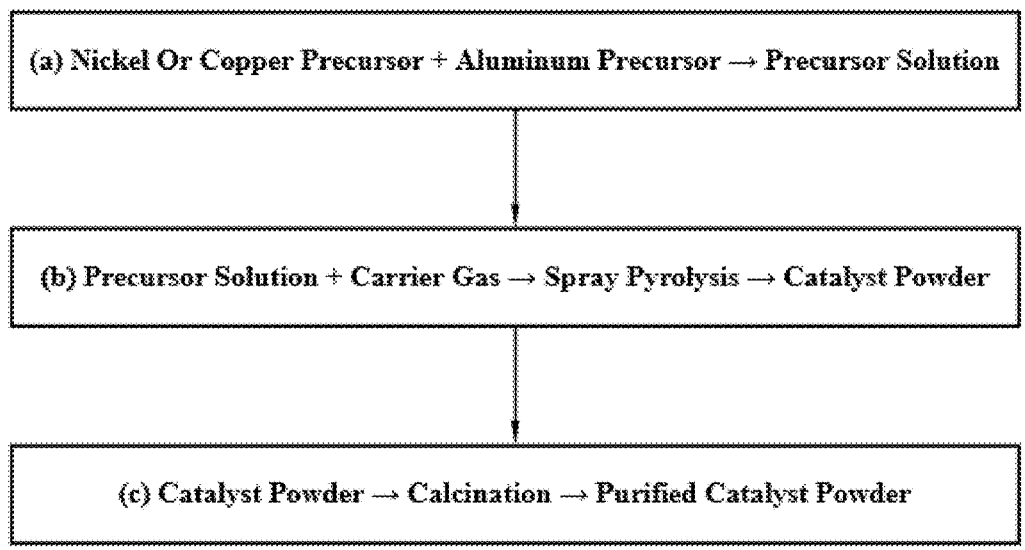
FIG. 1 is a schematic diagram showing a method of preparing a metal oxide catalyst according to one exemplary embodiment of the present invention.

Hereinafter, the present invention will be described in detail with reference to the accompanying drawings. However, it should be understood that the present invention can be implemented in various different forms, and is limited to the examples provided herein. In the drawings, descriptions of parts irrelevant to the detailed description are omitted in order to describe the present invention more clearly, and like numbers refer to like elements throughout the description of the figures.

In addition, it will be understood that when an element is referred to as being "connected" or "coupled" to another element throughout the specification, it can be directly connected or coupled to the other element or intervening elements may be present. In contrast, when an element is referred to as being "directly connected" or "directly coupled" to another element, there are no intervening elements present. Also, it will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Metal Oxide Catalyst

According to one aspect of the present invention, there is provided a metal oxide catalyst involved in a hydrogenation reaction in which a ketone is converted into an alcohol, wherein the metal oxide catalyst has a spinel structure represented by the following Formula 1:

$XAl_2O_4$     <Formula 1> wherein X represents nickel or copper.

The term "hydrogenation reaction" used in this specification refers to a reaction in which a hydrogen atom is added to a site at which two atoms in one molecule are connected via a carbonyl bond, or a hydrogen atom is added while cleaving a bond between the atoms in one molecule, and particularly to a reaction in which a ketone is converted into an alcohol.

Specifically, the hydrogenation reaction may occur by means of a catalyst following a dehydration reaction. In this reaction procedure, an alcohol may be produced.

The term "spinel structure" used in this specification refers fundamentally to a crystal structure of an oxide having an $XY_2O_4$ composition, and has as many as 8 X ions, 16 Y ion, and 32 O ions in a unit lattice in the isometric system. In general, the oxygen ions form face-centered cubic lattices so that X and Y ions can be introduced between the cubic lattices.

First, when X is nickel, the metal oxide catalyst may be nickel aluminate ($NiAl_2O_4$).

A content of the nickel in the metal oxide catalyst may be in a range of 20 to 65% by weight. Preferably, the content of the nickel may be in a range of 30 to 65% by weight, more preferably in a range of 35 to 61% by weight, and most preferably in a range of 45 to 57% by weight, but the present invention is not limited thereto. When the content of the nickel is out of this content range, production of byproducts may increase, and a ketone conversion rate and an alcohol yield may be lowered.

The nickel aluminate catalyst may have an average particle size of 100 to 1,000 nm, preferably 100 to 300 nm. When the average particle size of the nickel aluminate catalyst is less than 100 nm, it is difficult to control heat generation between the reactions. On the other hand, when the average particle size of the nickel aluminate catalyst is greater than 1,000 nm, the activity of the catalyst may be remarkably degraded due to a decrease in surface area of the catalyst.

Meanwhile, when X is copper, the metal oxide catalyst may be copper aluminate ($CuAl_2O_4$).

A content of the copper in the metal oxide catalyst may be in a range of 20 to 65% by weight, preferably in a range of approximately 30% by weight, but the present invention is not limited thereto. When the content of the copper is less than 20% by weight, production of the resulting byproducts may increase. On the other hand, when the content of the copper is greater than 65% by weight, the yield of methyl isobutyl carbinol may be lowered.

The copper aluminate catalyst may have an average particle size of 100 to 1,000 nm, preferably 300 to 1,000 nm. When the average particle size of the copper aluminate catalyst is less than 100 nm, it is difficult to control heat generation between the reactions. On the other hand, when the average particle size of the copper aluminate catalyst is greater than 1,000 nm, the activity of the catalyst may be remarkably degraded due to a decrease in surface area of the catalyst.

Method of Preparing Metal Oxide Catalyst

According to another aspect of the present invention, there is provided a method of preparing a metal oxide catalyst which includes (a) dissolving a nickel or copper precursor and an aluminum precursor in a polar solvent to prepare a precursor solution; (b) pyrolyzing the precursor solution while spraying the precursor solution into a reactor using a carrier gas so as to form a catalyst powder; and (c) transferring the catalyst powder to a storage tank, followed by calcining the catalyst powder in the storage tank to increase a surface area of the catalyst powder.

In step (a), the precursor solution may be prepared by dissolving a nickel or copper precursor and an aluminum precursor in a polar solvent.

A nitrate may be used as nickel, copper, and aluminum precursor materials to prepare the precursor solution, but the present invention is not limited thereto. In this case, one or more selected from the group consisting of a sulfate precursor, a chloride precursor, and a carbonate precursor may be used instead of the respective nitrate precursors.

In step (a), the polar solvent may be distilled water, but the present invention is not limited thereto. When the polar solvent is distilled water, an amount of impurities in the precursor solution may be minimized to improve the purity of copper aluminate and nickel aluminate catalysts as final products.

In step (b), the precursor solution may be pyrolyzed while spraying the precursor solution into a reactor using a carrier gas so as to form a catalyst powder.

Specifically, the carrier gas in step (b) may be air. Preferably, a pressure of the air may be in a range of 2 atm to 4 atm, more preferably 3 atm. When the pressure of the air is less than 2 atm, physical properties of the prepared catalyst do not reach the basic requirements for preparing an alcohol, resulting in degraded performance of the catalyst. On the other hand, when the pressure of the air is greater than 4 atm, high costs may become required and cause economic loss, and catalyst performance may be degraded due to formation of a solid solution and deformation of a crystal structure.

In step (b), the pyrolysis may be carried out at a temperature of 600 to 850° C., preferably a temperature of approximately 750° C. When the pyrolysis temperature is less than 600° C., it is impossible to obtain catalyst crystals suitable for the basic requirements for preparing an alcohol. On the other hand, when the pyrolysis temperature is greater than 850° C., the catalyst may be melted to form a solid solution, or a crystal structure of the catalyst may be randomly deformed. Therefore, the pyrolysis may be carried out in this temperature range to prepare a catalyst in which an active metal including copper or nickel is uniformly dispersed.

In step (c), after the catalyst powder is transferred to a storage tank, the catalyst powder may be calcined in the storage tank to increase a surface area of the catalyst powder. Also, purity of the catalyst may be improved, thereby improving selectivity and purity of an alcohol prepared using the catalyst.

The term "calcination" used in this specification refers to a heat treatment process for heating solids to cause pyrolysis or phase transition or to remove volatile components. In this specification, the term may be understood as the concept of encompassing a purification process of removing residual moisture and nitrates, which are included in the catalyst powder obtained after step (b) is completed, to obtain nickel aluminate and copper aluminate catalysts having improved purity, and as a process of activating the catalyst powder in the storage tank to improve stability of the catalyst.

In step (c), the calcination may be carried out at 350 to 450° C., preferably 380 to 420° C., and more preferably approximately 400° C., but the present invention is not limited thereto. When the calcination temperature is less than 350° C., desired levels of catalyst purity and alcohol selectivity may not be realized, compared to when the calcination is carried out only in step (b). On the other hand, when the calcination temperature is greater than 450° C., alcohol selectivity may be improved, but the yield of the alcohol may be remarkably lowered.

In step (c), the calcination may be carried out for 1 to 4 hours, preferably 1 to 3 hours. When the calcination is carried out for less than one hour, desired levels of catalyst purity and alcohol selectivity may not be realized, compared to when the calcination is carried out only in step (b). On the other hand, when the calcination is carried out for more than 4 hours, process efficiency and economic feasibility may be degraded due to the astringent activity of the catalyst.

Method of Preparing Alcohol

According to still another aspect of the present invention, there is provided a method of preparing an alcohol which includes allowing hydrogen to react with a ketone in the presence of the metal oxide catalyst to convert the ketone into an alcohol. A copper aluminate or nickel aluminate catalyst may be used when methyl isobutyl carbinol is prepared from methyl isobutyl ketone through a hydrogenation reaction. In this case, the methyl isobutyl ketone has a conversion rate of approximately 70 to 98%, and the methyl isobutyl carbinol has a selectivity of approximately 80 to 99.5%. Therefore, the conversion rate and the selectivity may be improved, compared to conventional preparation methods.

Regardless of a certain chemical theory, the production of the methyl isobutyl carbinol from the methyl isobutyl ketone may follow the following Scheme 1.

<Scheme 1>

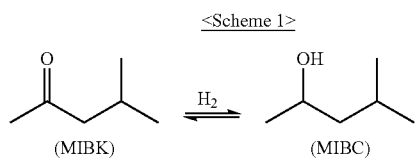

The reaction may be carried out at a temperature of 70 to 150° C., preferably a temperature of 85 to 130° C., and more preferably a temperature of 85 to 100° C., but the present invention is not limited thereto. When the reaction temperature is out of this temperature range, a conversion rate of the methyl isobutyl ketone and a yield of the methyl isobutyl carbinol may be remarkably lowered.

The reaction may be carried out at a pressure of 0.0 to 3.0 barg, preferably a pressure of 0.3 to 2.0 barg, and more preferably a pressure of 0.5 to 1.5 barg. When the pressure is less than 0.0 barg, a yield of the methyl isobutyl carbinol may be lowered. On the other hand, when the pressure is greater than 3.0 barg, the reactants methyl isobutyl ketone and hydrogen may be liquefied, resulting in degraded process efficiency.

The reaction may be carried out at a liquid hourly space velocity of 0.1 to 1.7 $hr^{-1}$, preferably a liquid hourly space velocity of 0.3 to 1.5 $hr^{-1}$, and more preferably a liquid hourly space velocity of 0.6 to 1.2 $hr^{-1}$. When the liquid hourly space velocity is less than 0.1 $hr^{-1}$, productivity may be degraded. On the other hand, when the liquid hourly space velocity is greater than 1.7 $hr^{-1}$, a time required to allow the methyl isobutyl ketone to react with the catalyst may be shortened, and thus an amount of unreacted materials may increase, resulting in a lowered yield of the methyl isobutyl alcohol.

The ketone and hydrogen may be allowed to react at a molar ratio of 1:4 to 8. For example, when the catalyst is copper aluminate, the ketone and hydrogen may be allowed to react at a molar ratio of 1:6 to 8 moles. When the molar ratio of the ketone and hydrogen is out of this range, selectivity of the methyl isobutyl carbinol may be degraded, and an amount of byproducts may increase.

Hereinafter, preferred embodiments of the present invention will be described in detail.

Example 1

A nickel salt and an aluminum salt were dissolved in distilled water and stirred to prepare a mixed solution. The prepared mixed solution was pyrolyzed while being sprayed into a reactor set to a temperature of 750° C. to obtain a powdery metal oxide. Thereafter, the powdery metal oxide was calcined at 400° C. to prepare a nickel aluminate catalyst having a nickel content of 35.4% by weight.

Example 2

A nickel aluminate catalyst having a nickel content of 45.8% by weight was prepared in the same manner as in Example 1, except that amounts of the nickel salt and the aluminum salt used were changed.

Example 3

A nickel aluminate catalyst having a nickel content of 56.8% by weight was prepared in the same manner as in Example 1, except that amounts of the nickel salt and the aluminum salt used were changed.

Example 4

A nickel aluminate catalyst having a nickel content of 60.8% by weight was prepared in the same manner as in Example 1, except that amounts of the nickel salt and the aluminum salt used were changed.

Example 5

A nickel aluminate catalyst having a nickel content of 62.9% by weight was prepared in the same manner as in Example 1, except that amounts of the nickel salt and the aluminum salt used were changed.

Example 6

A copper salt and an aluminum salt were dissolved in distilled water and stirred to prepare a mixed solution. The prepared mixed solution was pyrolyzed while being sprayed into a reactor set to a temperature of 750° C. to obtain a powdery metal oxide. Thereafter, the powdery metal oxide was calcined at 400° C. to prepare a copper aluminate catalyst having a copper content of 42.7% by weight.

Example 7

A copper aluminate catalyst having a copper content of 54.0% by weight was prepared in the same manner as in Example 6, except that amounts of the copper salt and the aluminum salt used were changed.

Comparative Example 1

A nickel aluminate catalyst having a nickel content of 28.8% by weight was prepared in the same manner as in Example 1, except that amounts of the nickel salt and the aluminum salt used were changed.

Comparative Example 2

A nickel aluminate catalyst having a nickel content of 70% by weight was prepared in the same manner as in Example 1, except that amounts of the nickel salt and the aluminum salt used were changed.

Comparative Example 3

A catalyst having a nickel element supported on an alumina ($Al_2O_3$) carrier was prepared using a known coprecipitation method. A content of nickel in the catalyst was 20% by weight.

Comparative Example 4

A copper aluminate catalyst having a copper content of 28.0% by weight was prepared in the same manner as in Example 6, except that amounts of the copper salt and the aluminum salt used were changed.

Comparative Example 5

A copper aluminate catalyst having a copper content of 65.4% by weight was prepared in the same manner as in Example 6, except that amounts of the copper salt and the aluminum salt used were changed.

Experimental Example 1: Analysis of Crystal Structure of Catalyst

Figure 2:
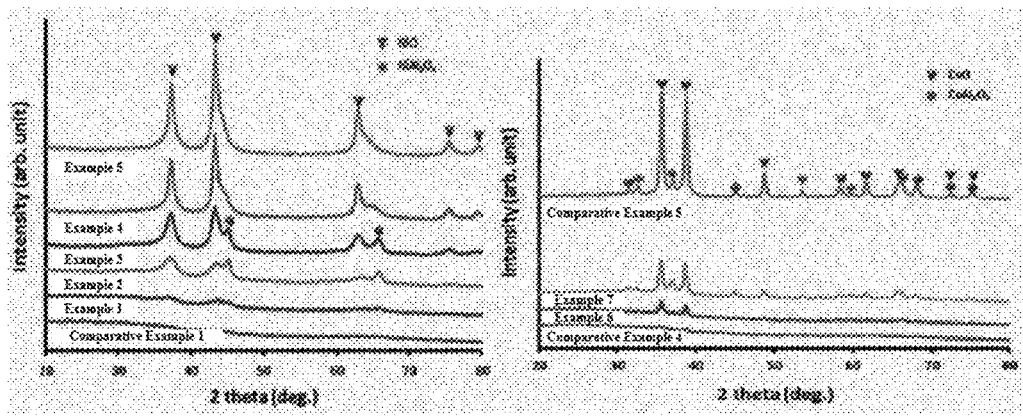
FIG. 2 is a diagram showing the X-ray diffraction (XRD) results of metal oxide catalysts prepared in examples and comparative examples of the present invention.

To check degrees of crystallinity of the nickel aluminate and copper aluminate catalysts prepared in Examples 1 to 7 and Comparative Examples 1, 4 and 5, an XRD assay was performed by an X-ray diffractometer using a Ni filter under conditions of 40 kV and 40 mA. The results are shown in FIG. 2. Referring to FIG. 2, the analysis showed that the crystal structure was a spinel structure regardless of the preparation conditions of the nickel aluminate and copper aluminate catalysts.

Experimental Example 2: Analysis of Particle Size and Shape of Catalyst

To analyze particle sizes and shapes of the metal oxide catalysts prepared in Examples 1 to 5 and Comparative Examples 1, 4 and 5, images were observed using transmission electron microscopy (TEM). The results are shown in FIG. 3.

Figure 3:
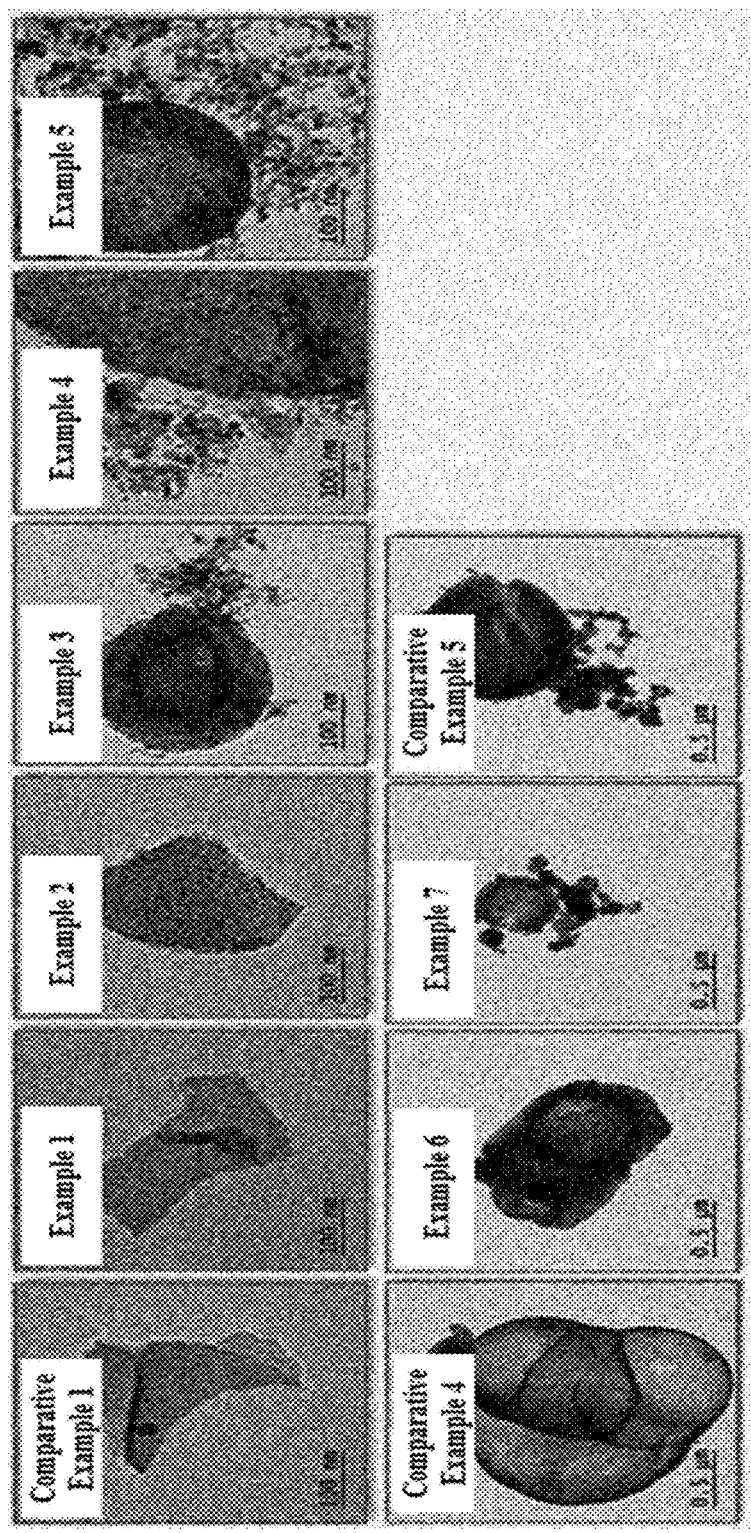
FIG. 3 shows a transmission electron microscope image of the metal oxide catalysts prepared in the examples and comparative examples of the present invention.

Referring to FIG. 3, the metal oxide catalysts of Examples 2 and 7 had a smaller particle size than the metal oxide catalysts of Comparative Examples 1 and 4, indicating that these results may support the results of Experimental Example 2.

Experimental Example 3: Evaluation of Activity of Nickel Aluminate Catalyst

Each of the catalysts prepared in Examples 1 to 5 and Comparative Examples 1 to 3 was introduced at a liquid hourly space velocity (LHSV) of 0.6 $hr^{-1}$, heated to 400° C. at atmospheric pressure, activated while allowing nitrogen and hydrogen to flow therethrough, and then cooled to a reaction temperature of 130° C. Thereafter, after a pressure was increased to 0.8 barg, each of the catalysts was activated while injecting hydrogen. Methyl isobutyl ketone (MIBK) and hydrogen were injected at a molar ratio of 1:8 to perform a hydrogenation reaction in the presence of the activated catalyst. In this way, methyl isobutyl carbinol (MIBC) was prepared. Then, the conversion rate of methyl isobutyl ketone, the selectivity of methyl isobutyl carbinol, the yield of methyl isobutyl carbinol, and the yield of byproducts were calculated using the following Equations 1 to 4, respectively. The results are listed in the following Table 1.

$$\text{Concersion Rate of Methyl Isobutyl Ketone (\%)} = \frac{\text{Weight of Reacted Methyl Isobutyl Ketone}}{\text{Weight of Injected Methyl Isobutyl Ketone}} \times 100 \quad \text{[Equation 1]}$$

$$\text{Selectivity of Methyl Isobutyl Carbinol (\%)} = \frac{\text{Weight of Produced Methyl Isobutyl Carbinol}}{\text{Weight of Reacted Methyl Isobutyl Ketone}} \times 100 \quad \text{[Equation 2]}$$

$$\text{Yield of Methyl Isobutyl Carbinol (\%)} = \frac{\text{Weight of Produced Methyl Isobutyl Carbinol}}{\text{Weight of Injected Methyl Isobutyl Ketone}} \times 100 \quad \text{[Equation 3]}$$

$$\text{Yield of By-products (\%)} = \text{Conversion Rate of Methyl Isobutyl Ketone} - \text{Yield of Methyl Isobutyl Carbinol} \quad \text{[Equation 4]}$$

TABLE 1

| Items | MIBK conversion rate (%) | MIBC selectivity (%) | MIBC yield (%) | Byproduct yield (%) |
|---|---|---|---|---|
| Example 1 | 87.4 | 99.7 | 87.1 | 0.3 |
| Example 2 | 91.1 | 99.5 | 90.6 | 0.5 |
| Example 3 | 91.8 | 98.5 | 90.4 | 1.4 |
| Example 4 | 91.0 | 97.8 | 89.0 | 2.0 |
| Example 5 | 91.0 | 98.0 | 89.1 | 1.9 |

TABLE 1-continued

| Items | MIBK conversion rate (%) | MIBC selectivity (%) | MIBC yield (%) | Byproduct yield (%) |
|---|---|---|---|---|
| Comparative Example 1 | 61.1 | 98.3 | 60.1 | 1.0 |
| Comparative Example 2 | 86.9 | 97.4 | 85.6 | 2.1 |
| Comparative Example 3 | 91.0 | 97.6 | 84.8 | 2.2 |

Referring to Table 1, it was revealed that the nickel aluminate catalysts of Examples 1 to 5 had an MIBK conversion rate of 85% or more, an MIBC selectivity of 97% or more and an MIBC yield of 89% or more, all of which were higher than those of the nickel aluminate catalysts of Comparative Examples 1 to 3, but one or more of the nickel aluminate catalysts of Comparative Examples 1 to 3 had an MIBK conversion rate, an MIBC selectivity, and an MIBC yield lower than those of Examples 1 to 5. As a result, it can be seen that all of the MIBK conversion rate, the MIBC selectivity, and the MIBC yield were realized in a balanced manner because the nickel aluminate catalysts of Examples 1 to 5 had remarkably improved catalytic activity, compared to the nickel aluminate catalysts of Comparative Examples 1 to 3.

Experimental Example 4: Evaluation of Activity of Copper Aluminate Catalyst

MIBC was prepared in the presence of each of the catalysts prepared in Examples 6 and 7 and Comparative Examples 4 and 5 in the same manner as in Experimental Example 3, and an MIBK conversion rate, an MIBC selectivity, an MIBC yield, and a byproduct yield were calculated using Equations 1 to 4, respectively. The results are listed in the following Table 2.

TABLE 2

| Items | MIBK conversion rate (%) | MIBC selectivity (%) | MIBC yield (%) | Byproduct yield (%) |
|---|---|---|---|---|
| Example 6 | 88.6 | 99.3 | 88.0 | 0.7 |
| Example 7 | 89.0 | 99.3 | 88.4 | 0.6 |
| Comparative Example 4 | 87.6 | 98.9 | 86.6 | 1.0 |
| Comparative Example 5 | 81.0 | 99.3 | 80.4 | 0.6 |

Referring to Table 2, it can be seen that all of the MIBK conversion rate, the MIBC selectivity, and the MIBC yield were realized in a balanced manner because the copper aluminate catalysts of Examples 6 and 7, which had a copper content of 42.7 to 54.0% by weight, had remarkably improved catalytic activity, compared to the copper aluminate catalysts of Comparative Examples 4 and 5.

Experimental Example 5: Evaluation of Activity of Catalyst According to Reaction Temperature To check the activity of the nickel aluminate catalyst and the copper aluminate catalyst prepared in Examples 2 and 7 according to the reaction temperature, respectively, each of the catalysts was introduced at a pressure of 0.8 barg and a liquid hourly space velocity of 0.6 hr$^{-1}$, and a hydrogenation reaction was carried out using a mixed gas, in which hydrogen and MIBK were mixed at a molar ratio of 1:8, while injecting air thereinto. MIBC was prepared at a temperature of 70 to 130° C., and an MIBK conversion rate, an MIBC selectivity, an MIBC yield, and a byproduct yield were calculated using Equations 1 to 4, respectively. The results are listed in the following Table 3.

TABLE 3

| Reaction temperature (° C.) | Conversion rate (%) | | MIBC selectivity (%) | | MIBC yield (%) | | Byproduct yield (%) | |
|---|---|---|---|---|---|---|---|---|
|  | Example 7 | Example 2 | Example 7 | Example 2 | Example 7 | Example 2 | Example 7 | Example 2 |
| 70 | 87.80 | 92.68 | 99.61 | 99.65 | 87.46 | 92.36 | 0.34 | 0.32 |
| 85 | 97.62 | 97.58 | 99.62 | 99.49 | 97.25 | 97.08 | 0.37 | 0.49 |
| 100 | 96.36 | 96.26 | 99.51 | 99.36 | 95.88 | 95.65 | 0.48 | 0.61 |
| 115 | 93.93 | 93.81 | 99.58 | 99.47 | 93.53 | 93.31 | 0.40 | 0.50 |
| 130 | 90.44 | 90.16 | 99.58 | 99.44 | 90.06 | 89.65 | 0.38 | 0.51 |

Referring to Table 3, it was revealed that the catalysts had an MIBC selectivity of 99% or more and a byproduct yield of 0.7% or less at a reaction temperature of 70 to 130° C.

Experimental Example 6: Evaluation of Activity of Catalyst According to Reaction Pressure To check the activity of the nickel aluminate metal oxide catalyst and the copper aluminate metal oxide catalyst prepared in Examples 2 and 7 according to the reaction pressure, each of the catalysts was introduced at a temperature of 85° C. and a liquid hourly space velocity of 0.6 hr$^{-1}$, and a hydrogenation reaction was carried out using a mixed gas, in which hydrogen and MIBK were mixed at a molar ratio of 1:8, while injecting air thereinto. MIBC was prepared at a pressure of 0 (atmospheric pressure) to 1.2 barg, and an MIBK conversion rate, an MIBC selectivity, an MIBC yield, and a byproduct yield were calculated using Equations 1 to 4, respectively. The results are listed in the following Table 4.

TABLE 4

| Reaction pressure | Conversion rate (%) | | MIBC selectivity (%) | | MIBC yield (%) | | Byproduct yield (%) | |
|---|---|---|---|---|---|---|---|---|
| (barg) | Example 7 | Example 2 | Example 7 | Example 2 | Example 7 | Example 2 | Example 7 | Example 2 |
| 0 (atmospheric pressure) | 96.50 | 96.20 | 99.36 | 99.57 | 95.84 | 95.79 | 0.61 | 0.41 |
| 0.3 | 96.90 | 96.99 | 99.42 | 99.64 | 96.38 | 96.63 | 0.56 | 0.35 |
| 0.8 | 97.62 | 97.58 | 99.62 | 99.49 | 97.25 | 97.08 | 0.37 | 0.49 |
| 1.2 | 98.10 | 98.06 | 99.52 | 99.43 | 97.60 | 97.50 | 0.47 | 0.32 |

Referring to Table 4, it was revealed that the catalysts had an MIBC yield of 96% or more and a byproduct yield of 0.7% or less at a reaction pressure of 0.3 to 1.2 barg.

Experimental Example 7: Evaluation of Activity of Catalyst According to the Molar Ratio of Reactants To check the activity of the nickel aluminate metal oxide catalyst and the copper aluminate metal oxide catalyst prepared in Examples 2 and 7 according to the molar ratio of the reactants, each of the catalysts was introduced at a temperature of 85° C., a pressure of 0.8 barg, and a liquid hourly space velocity of 0.6 $hr^{-1}$, and a hydrogenation reaction was carried out with a varying molar ratio of the reactants hydrogen and MIBK, ranging from 1:4 to 8, while injecting air thereinto. An MIBK conversion rate, an MIBC selectivity, an MIBC yield, and a byproduct yield were calculated using Equations 1 to 4, respectively. The results are listed in the following Table 5.

TABLE 5

| $H_2$/MIBK molar ratio | Conversion rate (%) | | MIBC selectivity (%) | | MIBC yield (%) | | Byproduct yield (%) | |
|---|---|---|---|---|---|---|---|---|
| | Example 7 | Example 2 | Example 7 | Example 2 | Example 7 | Example 2 | Example 7 | Example 2 |
| 4 | 95.39 | 96.96 | 99.36 | 99.68 | 94.78 | 96.66 | 0.61 | 0.31 |
| 6 | 96.83 | 96.24 | 99.47 | 99.57 | 96.32 | 95.83 | 0.51 | 0.42 |
| 8 | 97.62 | 97.58 | 99.62 | 99.49 | 97.25 | 97.08 | 0.37 | 0.49 |

Referring to Table 5, it was revealed that the catalysts had an MIBC selectivity of 99.3% or more and a byproduct yield of 0.7% or less when the molar ratio of the MIBK and hydrogen was in a range of 1:4 to 8.

Experimental Example 8: Analysis of Catalyst Using X-Ray Fluorescence Analyzer The contents of elements in the nickel aluminate metal oxide catalysts and copper aluminate metal oxide catalysts prepared in Examples 1 to 7 and Comparative Examples 1, 4 and 5 were analyzed using an X-Ray fluorescence (XRF) analyzer. The results are listed in the following Table 6.

TABLE 6

| | Element content (wt %) | | | | |
|---|---|---|---|---|---|
| Catalyst | Cu | Ni | Al | O | Total |
| Example 1 | — | 35.4 | 29.1 | 35.5 | 100 |
| Example 2 | — | 45.8 | 22.1 | 32.1 | 100 |
| Example 3 | — | 56.8 | 14.6 | 28.5 | 100 |
| Example 4 | — | 60.8 | 12.0 | 27.2 | 100 |
| Example 5 | — | 62.9 | 10.5 | 26.5 | 100 |
| Example 6 | 42.7 | — | 24.6 | 32.7 | 100 |
| Example 7 | 54.0 | — | 17.2 | 28.9 | 100 |
| Comparative Example 1 | — | 28.8 | 33.5 | 37.7 | 100 |
| Comparative Example 4 | 28.0 | — | 34.4 | 37.6 | 100 |
| Comparative Example 5 | 65.4 | — | 9.6 | 25.0 | 100 |

The metal oxide catalyst according to one exemplary embodiment of the present invention has a spinel structure and includes predetermined amounts of different metal components, and thus can be useful in improving yield and selectivity of an alcohol prepared through hydrogenation of a ketone.

Also, the method of preparing a metal oxide catalyst according to another exemplary embodiment of the present invention includes spray-pyrolyzing and calcining a precursor solution, and thus can be useful in improving the activity and purity of the metal oxide catalyst as well as productivity.

It should be understood that the effects of the present invention are not limited to the aforementioned effects, and encompasses all types of effects deducible from the configurations of the present invention disclosed in the detailed description and claims of the present invention.

It should be understood by those skilled in the art to which the present invention pertains that the description proposed herein is given for the purpose of illustration only, and various changes and modifications can be made to the aforementioned exemplary embodiments of the present invention without departing from the scope of the invention. Accordingly, the exemplary embodiments of the present invention are not intended to limit the scope of the invention but to describe the invention. For example, individual components described in an integral form may be implemented in a dispersed form, and individual components described in a dispersed form may also be implemented in an integral form.

The scope of the present invention is defined by the appended claims, and encompasses all modifications and alterations derived from meanings, the scope and equivalents of the appended claims.

What is claimed is:

1. A metal oxide catalyst involved in a hydrogenation reaction in which a ketone is converted into an alcohol, wherein the metal oxide catalyst has a spinel structure represented by the following Formula 1:

$XAl_2O_4$,  <Formula 1> wherein X represents nickel and a content of the nickel in the metal oxide catalyst is in a range of 35 to 65% by weight.

2. A metal oxide catalyst involved in a hydrogenation reaction in which a ketone is converted into an alcohol, wherein the metal oxide catalyst has a spinel structure represented by the following Formula 1:

$XAl_2O_4$,  <Formula 1> wherein X represents copper and a content of the copper in the metal oxide catalyst is in a range of 40 to 55% by weight.

3. The metal oxide catalyst of claim 1, wherein the metal oxide catalyst has an average particle size of 100 to 1,000 nm.

4. A method of preparing an alcohol, comprising:
allowing hydrogen to react with a ketone in the presence of the metal oxide catalyst defined in claim 1 to convert the ketone into an alcohol.

5. The method of claim 4, wherein the ketone is methyl isobutyl ketone.

6. The method of claim 5, wherein the alcohol is methyl isobutyl carbinol.

7. The method of claim 4, wherein the reaction is carried out at a temperature of 70 to 150° C.

8. The method of claim 4, wherein the reaction is carried out at a pressure of 0.0 to 3.0 barg.

9. The method of claim 4, wherein the reaction is carried out at a liquid hourly space velocity of 0.1 to 1.7 $hr^{-1}$.

10. The method of claim 4, wherein the ketone and the hydrogen are allowed to react at a molar ratio of 1:4 to 8.

11. The metal oxide catalyst of claim 2, wherein the metal oxide catalyst has an average particle size of 100 to 1,000 nm.

* * * * *